(12) United States Patent
Chan (10) Patent No.: US 7,972,564 B2
(45) Date of Patent: Jul. 5, 2011

(54) COMBINED LABYRINTHINE FLUID STERILIZING APPARATUS

(75) Inventor: Hak-Man Chan, Hong Kong (CN)

(73) Assignee: Solar City Limited, Kowloon Tong, Hong Kong (CN)

( * ) Notice: Subject to any disclaimer, the term of this patent is extended or adjusted under 35 U.S.C. 154(b) by 679 days.

(21) Appl. No.: 12/090,714

(22) PCT Filed: Aug. 22, 2006

(86) PCT No.: PCT/CN2006/002134
§ 371 (c)(1),
(2), (4) Date: Apr. 18, 2008

(87) PCT Pub. No.: WO2007/022709
PCT Pub. Date: Mar. 1, 2007

(65) Prior Publication Data
US 2010/0150793 A1    Jun. 17, 2010

(30) Foreign Application Priority Data

Aug. 22, 2005 (CN) .......................... 2005 1 0036660
Aug. 22, 2005 (CN) ...................... 2005 2 0063285 U
Nov. 1, 2005 (CN) ...................... 2005 2 0066371 U
Nov. 22, 2005 (CN) ...................... 2005 2 0067727 U
Apr. 21, 2006 (CN) .......................... 2006 1 0035126
Apr. 21, 2006 (CN) ...................... 2006 2 0058051 U
Aug. 22, 2006 (WO) ................ PCT/CN2006/002134

(51) Int. Cl.
*A61L 9/00* (2006.01)
(52) U.S. Cl. ........ 422/120; 422/121; 422/122; 422/124; 422/186.3; 204/157.3
(58) Field of Classification Search ............... 422/186.3, 422/24, 120, 121, 122, 124; 204/157.3
See application file for complete search history.

(56) References Cited

U.S. PATENT DOCUMENTS

2003/0146082 A1* 8/2003 Gibson et al. .............. 204/157.3
(Continued)

FOREIGN PATENT DOCUMENTS

CN            87207074 U       3/1988
(Continued)

OTHER PUBLICATIONS

Derwent Abstract for CN 1306877 A, Published Aug. 2001; Inventor: Yu.*

*Primary Examiner* — Sean E Conley
(74) *Attorney, Agent, or Firm* — Hoffman & Baron, LLP (57) ABSTRACT

The present invention provides a combined labyrinthine fluid sterilizing apparatus, comprising a chamber having an inlet and an outlet as well as a blower/fan provided in the chamber. Ultraviolet lamps are mounted in the lumen of the chamber. The lumen of the chamber is divided by a plurality of bafflers having pores. The pores in the adjacent bafflers are arranged to stagger up and down or from side to side. A mesh plate is provided at the pore. The top and bottom plates of the chamber can be flipped open. The baffler is inserted in the slots in the inner side of the front and back plates. The top and bottom plates have the pore and a cover plate which are both covered by a shield. At least one of the bafflers has a pore, and is provided with a one-way openable valve. The blower is mounted at the pore of the baffler. The chamber and the bafflers are coated with a layer of titanium dioxide. According to the present invention, it is possible to add, remove, or replace the baffler, the filter mesh, the blower or the purifying accessories and the like. The one-way openable valve can prevent the polluted water or air from flowing backwards. Further the to and fro winding disinfecting and sterilizing path prolongs the disinfecting and sterilizing process and increases the duration. With the photocatalytic effect of titanium dioxide, the organic substances are effectively decomposed, the dirt is eliminated, and deodorization and sterilization achieved. As a result, an ideal effect of disinfection and sterilization is achieved.

11 Claims, 9 Drawing Sheets

U.S. PATENT DOCUMENTS

2004/0013583 A1  1/2004  Burkhardt
2008/0031783 A1* 2/2008 Briggs et al. .................. 422/121

FOREIGN PATENT DOCUMENTS

| CN | 2212004 Y | 11/1995 |
|---|---|---|
| CN | 2235283 Y | 9/1996 |
| CN | 2524473 Y | 12/2002 |
| CN | 2598626 Y | 1/2004 |
| CN | 2642314 Y | 9/2004 |
| CN | 2643891 Y | 9/2004 |
| CN | 2709225 Y | 7/2005 |
| CN | 2725759 Y | 9/2005 |

* cited by examiner

COMBINED LABYRINTHINE FLUID STERILIZING APPARATUS

This application claims priority based on an International Application filed under the Patent Cooperation Treaty Application No. PCT/CN2006/002134, filed on Aug. 22, 2006; Chinese Application No. 200510036660.6, filed on Aug. 22, 2005; Chinese Application No. 200520063285.X, filed on Aug. 22, 2005; Chinese Application No. 200520066371.6 filed on Nov. 1, 2005; Chinese Application No. 200520067727.8 filed on Nov. 22, 2005; Chinese Application No. 200610035126.8 filed on Apr. 21, 2006; and Chinese Application No. 200620058051.0 filed on Apr. 21, 2006 which are all incorporated herein by reference.

TECHNICAL FIELD

The present invention generally relates to a purifying apparatus for gas and/or sewage, in particular, to a combined labyrinthine fluid sterilizing apparatus which, using ultraviolet light and a photocatalyst made by titanium dioxide ($TiO_2$), is capable of disinfecting and sterilizing indoor polluted air or polluted liquid.

BACKGROUND ART

With the raising of living standard, the expectation of people on the environment sanitation becomes increasingly high. However, the modern industrialization, while satisfying the growing demands of people for material well-being, brings about, as the byproducts, polluted water, polluted air as well as emerging virus and bacteria which more and more severely threaten human health and hinder the development of the society. On the other hand, with the development of science, people have recognized that titanium dioxide ($TiO_2$) is a kind of photocatalyst which has many excellent functions such as anti-pollution, deodorization, anti-bacteria, sterilizing, purifying water quality and atmosphere, decomposing dirt and harmful chemicals and so on and can be used as an effective technical means for protecting the ecological environment. In the course of research, it is found that titanium dioxide ($TiO_2$) can generate extremely formidable effect of oxygenolysis after being irradiated by sunlight (ultraviolet light), in particular, when irradiated by the UVC type of ultraviolet light it can generate sterilization effect many times more powerful than those generated by other types of ultraviolet lights. Currently, people are paying serious attention to such a miraculous photocatalyst, titanium dioxide ($TiO_2$). A light interference color film which may be formed on the surface of various materials can effectively decompose organic substances, eliminate dirt, deodorize and resist bacteria. The photocatalyst is used for manufacturing a fluid purifying apparatus with the functions such as deodorization, sterilization and the like. The use of titanium dioxide ($TiO_2$) to disinfect, sterilize and purify polluted water and air has become the question with which people are getting more and more concerned. To achieve this, many endeavours have been made. There are now a great variety of disinfection, sterilization and purification devices for water or air using titanium dioxide ($TiO_2$). The configurations of such devices are set and assembled within the factory. As such, their disinfecting and filtering capabilities have been fixed and cannot be adjusted by adding, removing or replacing the filter mesh, blower/fan, or purifying accessories and the like according to the size of the particular space requiring disinfection and the degree of pollution of the environment.

SUMMARY OF THE INVENTION

The objective of the present invention is to provide a combined labyrinthine fluid sterilizing apparatus which can add, remove or replace the filter mesh, blower/fan, or purifying accessories and the like according to the size of the space requiring disinfection and the degree of pollution of the environment.

To achieve the above objective, it is provided, according to one aspect of the present invention, a combined labyrinthine fluid sterilizing apparatus, comprising a chamber having an inlet and an outlet as well as a blower/fan mounted in the chamber, wherein ultraviolet lamps are mounted in the lumen of the chamber, characterized in that the lumen of said chamber between the inlet and the outlet is divided by at least one baffler having pores, the baffler is inserted in slots corresponding thereto provided in the inner side of the front and back plates of the chamber or the baffler without pores is only inserted into one slot provided in the left wall, the right wall, the ceiling or the base of the chamber and is shorter in length than the distances between the left and right walls and between the ceiling and the base; the top plate and/or bottom plate of the chamber have a hinge structure which is capable of being flipped open; and the baffler is inserted in the slots corresponding thereto provided in the inner side of the front and back plates of the chamber.

Preferably, at least one said baffler is inserted in the slots corresponding thereto provided in the inner side of the front and back plates of the chamber wherein the baffler has pores which are provided with photocatalyst filter meshes of titanium dioxide.

Preferably, at least one said baffler includes a plurality of bafflers wherein the baffler, without pores, is merely inserted in one slot in the left wall, the right wall, the ceiling or the base and is shorter in length than the distances between the left wall and the right wall or between the ceiling and the base of the chamber lumen, and the left and right bafflers or the upper and lower bafflers are staggered with an interval forming a winding disinfecting path; and wherein the baffler is coated with a layer of titanium dioxide and ultraviolet lamps are mounted on the ceiling and at the base of the chamber.

Preferably, the pore of the baffler is positioned at the upper portion or the lower portion of the baffler and the pores in adjacent bafflers are staggered up and down.

Preferably, the pore of the baffler is positioned at the left portion or the right portion of the baffler and the pores in adjacent bafflers are staggered laterally.

Preferably, the ultraviolet lamps are mounted on the inner wall of the chamber with the lamp tube horizontally inserted in the upper and/or lower midway-indentations of the bafflers.

Preferably, the slot of the baffler is an inclined slot, a vertical slot or a horizontal slot.

Preferably, the top plate and/or the bottom plate of the chamber are provided with pores and a cover plate, and the pores and the cover plate are covered by a shield fixed to the top plate and/or the bottom plate wherein the cover plate has a raised-cover plate screw passing through the shield.

Preferably, the pore in one of the bafflers is provided with a one-way openable valve.

Preferably, the blower/fan is mounted at the pore of one baffler.

Preferably, the middle portion of the baffler is in wave shape.

Preferably, the baffler is coated with a layer of titanium dioxide or is on its surface distributed with titanium dioxide nails.

Preferably, the blower/fan is of the types of a pig cage, a blade, a pump or any type appropriate in the circumstances. It can be used solely for either air suction or water pumping; besides, it may be provided as a double layer structure with the upper layer for air suction and the lower layer for water pumping.

Preferably, the ultraviolet lamp is a UVC or UV-B or UV-A ultraviolet lamp or the combination thereof.

Preferably, the lower portion of the chamber is further provided with a titanium dioxide filter which is connected to the outlet of the disinfecting chamber and also mounted in the chamber.

Preferably, the lower portion of the chamber is further provided with a nano filter which is connected to the outlet of the titanium dioxide filter and also mounted in the chamber.

Preferably, the lower portion of the chamber is further provided with an active carbon filter which is connected to the outlet of the titanium dioxide filter and also mounted in the chamber.

Preferably, the slot of the baffler is an inclined slot, a vertical slot or a horizontal slot.

According to another aspect of the present invention, it is provided a water-quality disinfecting and sterilizing apparatus comprising a chamber as well as water pipes and ultraviolet lamps provided in the chamber, characterized in that the water pipes are made of transparent quartz glass or material penetrable by ultraviolet light and are arranged in at least two rows, in each of which the water pipes extend and wind to and fro, and in that the ultraviolet lamps are mounted on the inner wall of the chamber, alternating between the water pipes.

Preferably, at least one metal bar or chain coated with a layer of titanium dioxide is located in the water pipes.

Preferably, the water pipes are on their inner wall coated with a layer of titanium dioxide and the chamber is on its inner wall coated with a light reflective layer.

Preferably, the outlets of the water pipes are connected with the filter which is also mounted in the chamber and the filter is provided at its lower portion with an ultraviolet lamp.

Preferably, the outlets of the water pipes are connected with the filter which is also mounted in the chamber and the filter is provided at its upper portion with an ultraviolet lamp.

According to a further aspect of the present invention it is provided a photocatalytic disinfecting and sterilizing cabinet which comprises a chamber and a door, characterized in that the chamber is on its inner wall surface coated with a titanium dioxide layer and is provided therein with an ultraviolet lamp.

Preferably, the ultraviolet lamp is a UVC ultraviolet lamp which is mounted in the top portion of the chamber and protected by a grid.

The beneficial effects of the present invention are as follows. Owing to the openable hinge structure of the top plate and/or bottom plate of the chamber in the present invention and the bafflers inserted in the slots corresponding thereto provided in the inner side of the front and back plates of the chamber, it is possible to open the top plate and add, remove or replace the bafflers, i.e. the filter mesh, blower/fan or purifying accessories etc., depending on the specific size of the space requiring disinfection and the degree of pollution of the environment; the stagger arrangement of the pores of the adjacent bafflers extends the flowing process and increases the flowing time of the polluted water or air in the course of winding through the bafflers wherein due to the sufficient ultraviolet irradiation and the effect of titanium dioxide which can be found everywhere, the organic substances in the polluted water and air are effectively decomposed, the dirt eliminated, and the deodorization and sterilization achieved.

Moreover, the photocatalytic disinfecting and sterilizing apparatus according to the present invention is additionally provided with a variety of filters so as to achieve more ideal effects of disinfection and sterilization. The pore of one of the bafflers is provided with a one-way openable valve which prevents the air or water from flowing backwards in case of power breakdown resulting from machinery failure. In addition, the present invention provides a disinfecting and sterilizing apparatus for liquid, more specifically for drinking water, which, by prolonging the disinfecting and sterilizing path through which the liquid flows, can more effectively disinfect and sterilize liquid and particularly the drinking water. The present invention provides a photocatalytic disinfecting and sterilizing cabinet which comprises a chamber and a door and which, through the titanium dioxide layer coated on the inner surface of the chamber and the ultraviolet lamps mounted in the chamber, effectively disinfects and sterilizes and is more suitable for the sterilization of dishware.

BRIEF DESCRIPTION OF THE DRAWINGS

Hereinafter the present invention is further described in detail in conjunction with the figures and embodiments.

Figure 1:
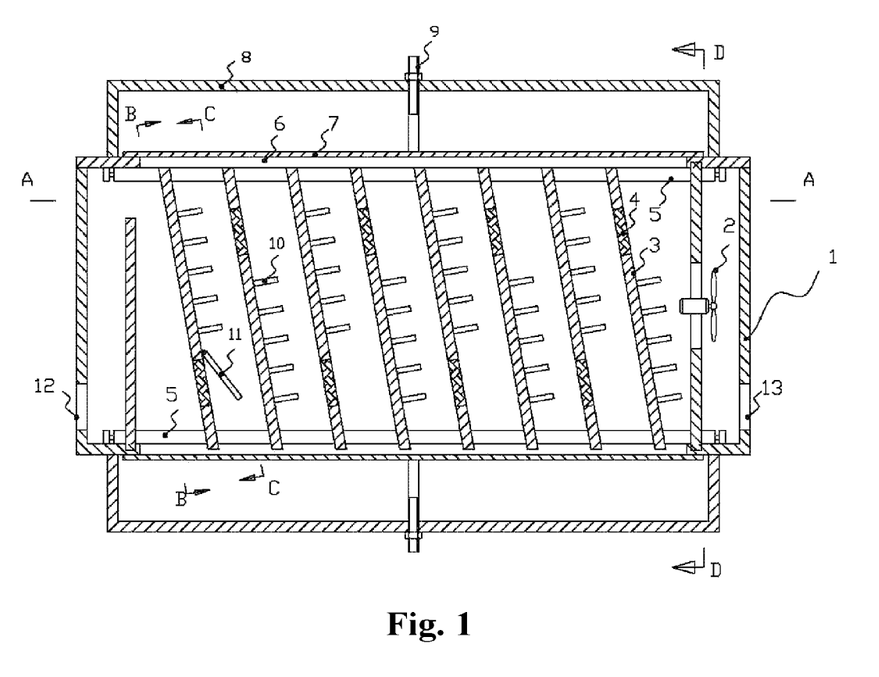
FIG. 1 is the constructional sectional view of the first embodiment of the present invention.
Figure 2:
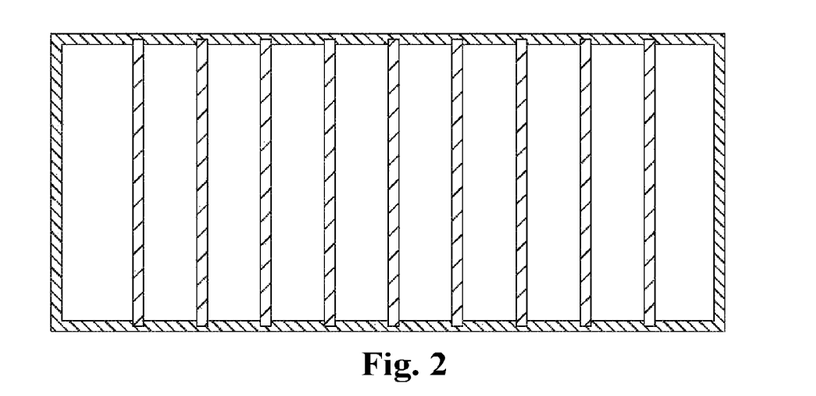
FIG. 2 is the sectional view taken along the line A-A in FIG. 1.
Figure 3:
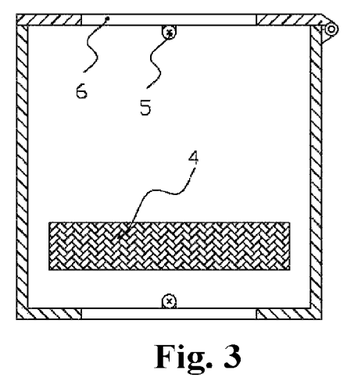
FIG. 3 is the sectional view taken along the line B-B in FIG. 1.
Figure 4:
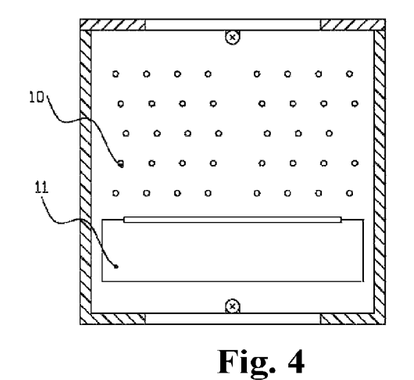
FIG. 4 is the sectional view taken along the line C-C in FIG. 1.
Figure 5:
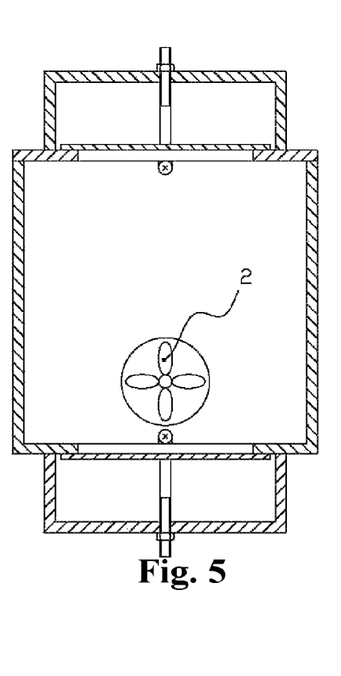
FIG. 5 is the sectional view taken along the line D-D in FIG. 1.
Figure 6:
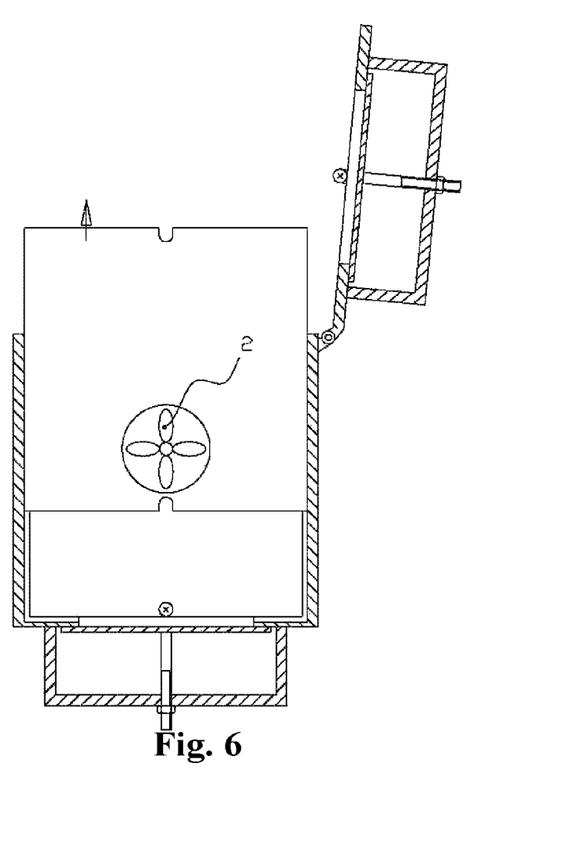
FIG. 6 is the sectional view of the first embodiment wherein the cover plate is opened.
Figure 7:
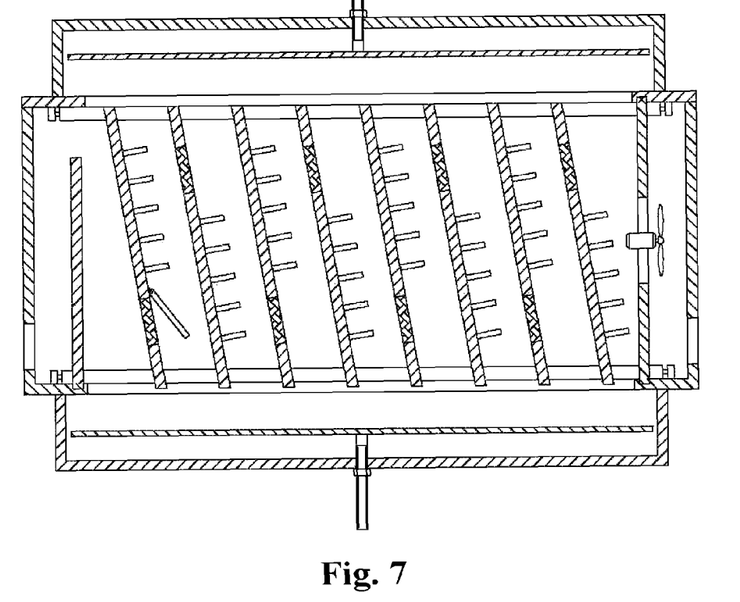
FIG. 7 is the sectional view of the first embodiment wherein the top plate is opened and the baffler is removed.

IN FIGURES 1 chamber,
2 blower/fan or water pump, 3 baffler,
4 filter mesh,
5 UVC type ultraviolet lamp,
6 pore in the top plate or the bottom plate,
7 cover plate,
8 shield,
9 raised-coverplate screw,
10 titanium dioxide nail,
11 one-way openable valve,
12 chamber inlet,
13 chamber outlet,
14 titanium dioxide filter,
15 nano filter,
16 active carbon filter,
17 disinfecting cavity,
18 air filter mesh,
20 water pipe,
22 light-reflecting layer,
24 filter,
26 metal bar or chain,
28 titanium dioxide coated bar in the inner wall of the water pipe,
30 titanium dioxide layer/coating,
32 grid,
34 dishware,
36 the position where the door is opened.

DESCRIPTION OF PREFERRED EMBODIMENTS

In the scope of the present invention, the term "blower/fan" is intended not only to refer to the suction device used during the gas treatment but also to refer to a variety of other gas and/or liquid suction devices applicable for treating gas and/or liquid, such as different types of blower/fan, water pumps and the like. The blower/fan may be of the type of a pig cage or a blade type water pump or any type of blower/fan appropriate in the circumstances which can be used solely for either air suction or water pumping and may also be provided as a double layer structure with the upper layer for air suction and the lower layer for water pumping.

More specifically, the present invention provides a combined labyrinthine fluid sterilizing apparatus as follows.

The combined labyrinthine fluid sterilizing apparatus according to the present invention comprises a chamber having an inlet and an outlet as well as a blower/fan mounted in the chamber, the blower/fan and the chamber are coated with a titanium dioxide layer, and the lumen of the chamber is provided with ultraviolet lamps therein, characterized in that the lumen of the chamber between the inlet and the outlet is divided by at least one baffler, the baffler having pores is inserted in the slots corresponding thereto provided in the inner side of the front and back plates of the chamber and alternatively the baffler having no pore is inserted in only one slot in the left wall, right wall, the ceiling or the base of the chamber and the baffler is shorter in length than the distance between the left and right walls or between the ceiling and the base and is on its surface coated with a titanium dioxide layer; and the top plate and/or bottom plate of the chamber have a hinge structure capable of being flipped open.

In one embodiment, at least one baffler is inserted in the slots corresponding thereto provided in the inner side of the front and back plates of the chamber wherein the baffler has pores and titanium dioxide photocatalyst filter mesh is provided at the pores.

In another embodiment, said at least one baffler includes a plurality of bafflers which, without pores, are inserted in one slot in the left wall, the right wall, the ceiling or the base of the chamber and are shorter in length than the distance between the left and right walls or between the ceiling and the base of the lumen wherein the left and right bafflers or the upper and lower bafflers are staggered with interval forming a to and fro winding disinfecting path; the baffler is on its surface coated with a titanium dioxide layer; and ultraviolet lamps are provided on the ceiling and the base of the chamber.

In another embodiment, the baffler has the pore in the upper or the lower portion and the pores in the adjacent bafflers are arranged to stagger up and down.

In another embodiment, the baffler has the pore in the left or the right portion and the pores in the adjacent bafflers are arranged to stagger laterally.

In another embodiment, the ultraviolet lamps are mounted on the inner wall of the chamber with the lamp tubes horizontally inserted in the upper and/or lower midway-indentations in the bafflers.

In another embodiment, the slot of the baffler is an inclined slot, a vertical slot or a horizontal slot.

In another embodiment, the top plate and/or the bottom plate of the chamber are provided with pores and a cover plate which are covered by a shield fixed to the top plate and/or the bottom plate wherein the cover plate is provided with a raised-coverplate screw passing though the shield.

In another embodiment, the pore in one of the bafflers is provided with a one-way openable valve.

In another embodiment, the blower/fan is provided at the pore of one baffler.

In another embodiment, the middle portion of the baffler is in wave shape.

In another embodiment, the baffler is coated with a titanium dioxide layer or on its surface distributed with titanium dioxide nails.

In another embodiment, the blower/fan, which is of the type of a pig cage, a blade type water pump or any type of blower/fan appropriate in the circumstances, can be used solely for either air suction or water pumping and may be provided as a double layer structure with the upper layer for air suction and the lower layer for water pumping.

In another embodiment, the ultraviolet lamp is a UVC or UV-B or UV-A type ultraviolet lamp or the combination thereof.

In another embodiment, the lower portion of the chamber is further provided with a titanium dioxide filter which is connected to the outlet of the disinfecting chamber and also mounted in the chamber.

In another embodiment, the lower portion of the chamber is further provided with a nano filter which is connected to the outlet of the titanium dioxide filter and also mounted in the chamber.

In another embodiment, the lower portion of the chamber is further provided with an active carbon filter which is connected to the outlet of the titanium dioxide filter and also mounted in the chamber.

In another embodiment, the slot of the baffler is an inclined slot, a vertical slot or a horizontal slot.

According to another aspect of the present invention, it is provided a water-quality disinfecting and sterilizing apparatus comprising a chamber as well as water pipes with ultraviolet lamps provided in the chamber, characterized in that the water pipes are made of transparent quartz glass or material penetrable by ultraviolet light and are arranged in at least two rows in each of which the water pipes extend and wind to and fro, and in that the ultraviolet lamps are provided in the inner wall of the chamber, alternating between the water pipes.

In one embodiment, at least one metal bar or chain coated with a titanium dioxide layer is positioned in the water pipe.

In another embodiment, the water pipe is on its inner wall partially coated with a titanium dioxide layer and the chamber is on its inner wall coated with a light-reflecting layer.

In another embodiment, the outlet of the water pipe is connected with the filter which is also mounted in the chamber and the filter is provided at its lower portion with an ultraviolet lamp.

In another embodiment, the outlet of the water pipe is connected with the filter which is also mounted in the chamber and the filter is provided at its upper portion with an ultraviolet lamp.

According to a further aspect of the present invention, it is provided a photocatalytic disinfecting and sterilizing cabinet which comprises a chamber and a door, characterized in that the chamber is on its inner wall surface coated with a titanium dioxide layer and is provided therein with ultraviolet lamps.

In one embodiment, the ultraviolet lamp is a UVC type ultraviolet lamp which is mounted in the top portion of the chamber and protected by a grid. The following description is based on the accompanying figures, which serves to facilitate a better understanding of the present invention and is for the purpose of illustration only and not for limiting the present invention.

As shown in FIGS. 1-6, according to the first embodiment of the present invention, the combined labyrinthine fluid sterilizing apparatus comprises a chamber 1 with an inlet 12 and an outlet 13 as well as a blower/fan 2 provided in the chamber, the blower/fan and the chamber are coated with a titanium dioxide layer, the lumen of the chamber between the inlet and the outlet is divided by eight bafflers 3, the baffler has a pore in its upper portion or the lower portion, the pores in the adjacent bafflers are arranged to stagger up and down, a titanium dioxide photocatalyst filter mesh 4 is provided at the pore, the baffler is on its surface coated with a titanium dioxide layer and/or distributed with titanium dioxide nails 10; the top plate and the bottom plate 6 of the chamber have a hinge structure capable of being flipped open; the baffler 3 is inserted in the corresponding inclined baffler-slots in the inner side of the front and back plates of the chamber such that it is possible to add, remove or replace the filter mesh, the blower/fan, or the purifying accessories etc. depending on the particular size of the space requiring disinfection and sterilization and the degree of pollution of the environment. Alternatively, the blower/fan may be provided at the pore of the baffler facilitating the replacement and maintenance thereof; the UVC ultraviolet lamp 5 is mounted mid-way between the inner side of the top plate and the bottom plate of the chamber with the light tube horizontally inserted in the upper and lower midway-indentations of the bafflers; the top and bottom plates are provided therein with big openings 6 and cover plates 7 which are covered by the shield 8 fixed to the top plate and the bottom plate wherein the cover plate has the raised-cover plate screw 9 passing through the shield and if necessary the cover plate can be opened to allow massive air or sewage to enter from the inlet 12 directly through the upper and lower paths at the top plate and the bottom plate; the pore in one of the plurality of bafflers is provided with the one-way openable valve 11 such that the sewage or the air can only flow in one direction which effectively prevents back tracking resulting from closure of the apparatus, particularly in order that the bacteria/virus trapped in the filter mesh cannot return from this apparatus to the disinfected and sterilized space.

Figure 8:
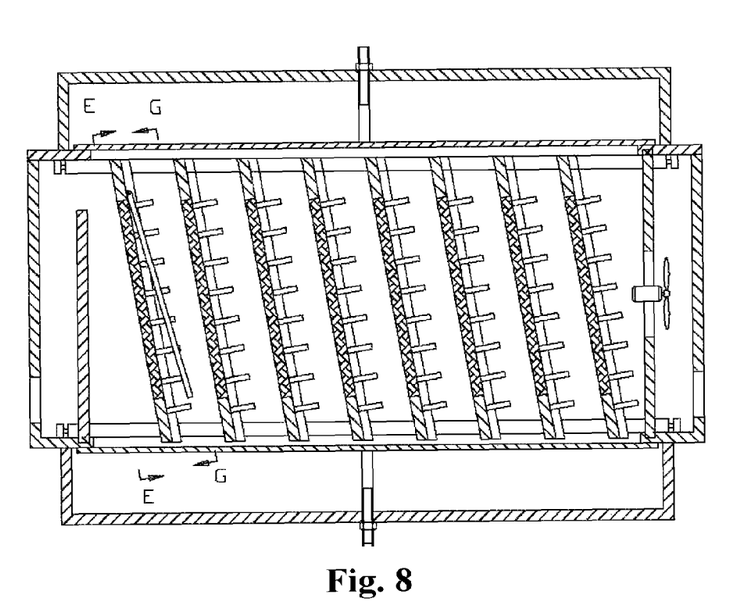
FIG. 8 is the constructional sectional view of the second embodiment.
Figure 9:
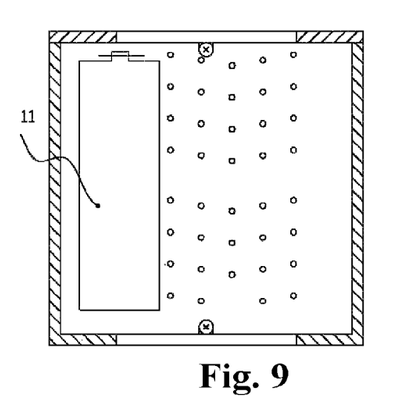
FIG. 9 is the sectional view taken along the line E-E in FIG. 8.
Figure 10:
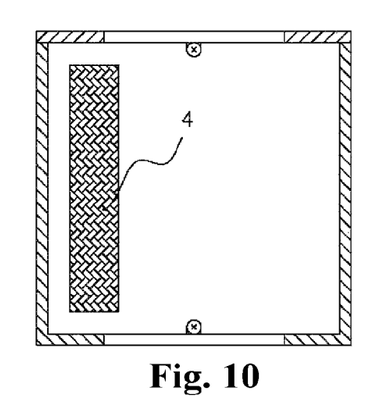
FIG. 10 is the sectional view taken along the line G-G in FIG. 8.

The second embodiment of the present invention is shown in FIGS. 8-10. It is essentially the same with the above embodiment except that the baffler has the pore in its left or right portion and the pores in the adjacent bafflers are arranged to stagger from side to side so as to simultaneously treat sewage and polluted air wherein the sewage/liquid passes through the lower portion of the pore while the polluted air passes through the upper portion of the pore. The present embodiment is particularly applicable to underground drainage pipes and can effectively decompose organic substances contained in the sewage and air, eliminate dirt, deodorize, disinfect and sterilize simultaneously.

Figure 11:
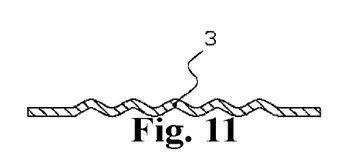
FIG. 11 is the sectional view of the baffler in wave shape.

In addition, the middle portion of the baffler may be made in wave shape to increase the contact of the water and air with the baffler, see FIG. 11. A filter mesh may also be provided at the inlet and outlet of the chamber, see FIGS. 11 and 12.

It may further be provided on the baffler 3 with a positive ion, negative ion, or ionization generator.

Figure 12:
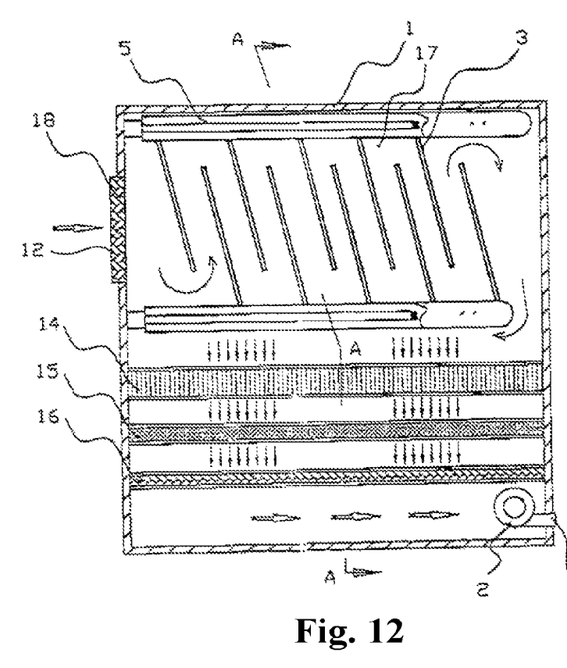
FIG. 12 is the constructional sectional view of the third embodiment of the present invention.
Figure 13:
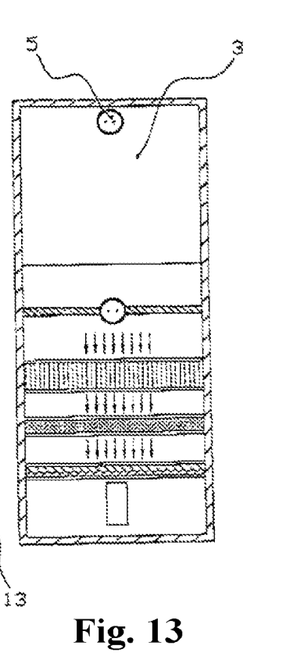
FIG. 13 is the sectional view of the third embodiment of the present invention taken along the line A-A in FIG. 12.

As shown in FIGS. 12 and 13, in the third embodiment (another variant) of the present invention, the apparatus comprises a chamber 1 as well as a disinfecting and sterilizing cavity 17 and a blower/fan 2 both provided in the chamber, wherein the chamber 1 has an inlet 12 which is provided with an air filter mesh 18 carrying active carbon and an outlet 13 where the blower/fan 2 is mounted such that the polluted water or gas is sucked into the disinfecting and sterilizing cavity 17 from the chamber inlet by the blower/fan and then exits through the outlet; the disinfecting and sterilizing cavity is arranged such that the baffler, without pores, is only inserted in one slot in the top plate and the bottom plate of the chamber and is shorter in length than the height between the ceiling and the base of the lumen, that is, a gap remains between the upper baffler and the base and at the same time another gap exists between the lower baffler and the ceiling, and also the upper baffler and the lower baffler are staggered at intervals which, together with the front and back walls, form a to-and-fro winding disinfecting and sterilizing path; the baffler is on its surface coated with a titanium dioxide layer; and a UVC type ultraviolet lamp 5 is mounted on the ceiling and the base. The lamp tube is horizontally inserted between the disinfecting and sterilizing paths. The outlet of the disinfecting and sterilizing cavity 17 is connected with an existing titanium dioxide filter 14 which is also mounted in the chamber and the titanium dioxide filter is in turn connected to an existing nano filter 15 which is an air filter core comprising a nano sterilizing material or other type of sterilizing material. The selected sterilizing material may be at least one of Dichlorodimethylhydantoin (DDH), Dibromodimethylhydantoin (DBDMH), Bromochlorodimethylhydantoin (BCDMH), Trichloro-isocyanuric acid, Sodium dichloro-isocyanurate, Bromochloro-isocyanuric acid, Tetrachloroglycoluril, Bromochloroglycoluril. Afterwards, the polluted water or gas passes through the active carbon filter 16 again and is sucked out of the chamber outlet by the blower/fan after having been repeatedly filtered, disinfected and sterilized.

If the combined labyrinthine fluid sterilizing apparatus according to the present invention is miniaturized, it is possible after removing the blower/fan to hang the apparatus directly at the vent of an air-conditioner and the like. If the said apparatus is microminiaturized, it can be made into the form of a mask.

If the combined labyrinthine fluid sterilizing apparatus according to the present invention is scaled up, suitable applications include hospitals, urban drainage pipelines, sealed breeding farms and so on and polluted liquid and gas can be treated simultaneously.

The combined labyrinthine fluid sterilizing apparatus according to the present invention may be used for air disinfection, sterilization and purification, such as air-conditioners etc. or as the disinfecting and sterilizing apparatus for sanitary sewage or breeding farm sewage.

In addition, the present invention provides for further variant solutions.

One variant solution of the present invention is shown in FIGS. 14 through 20. It is an apparatus specially used for disinfecting and sterilizing liquid, and particularly suitable for drinking water.

Figure 14:
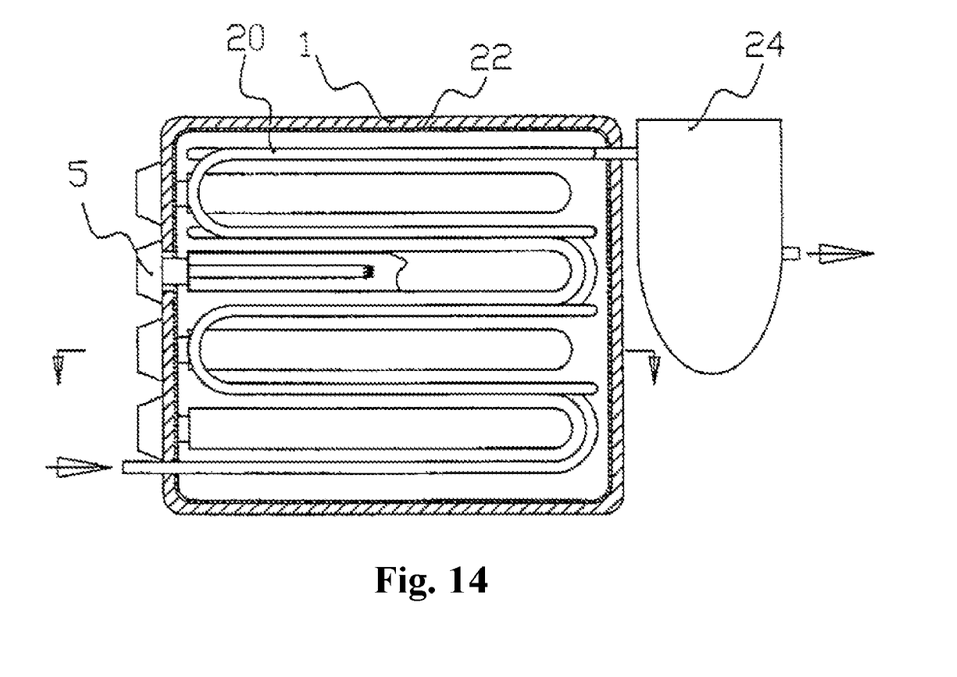
FIG. 14 is the constructional sectional view of the fourth embodiment of the present invention.
Figure 15:
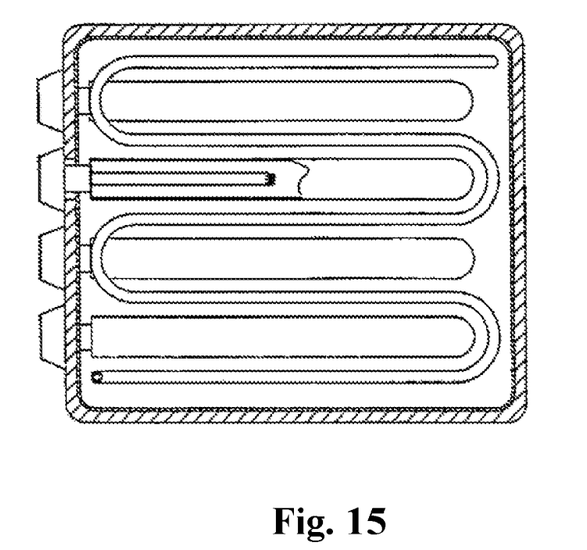
FIG. 15 is the sectional view taken along the line A-A in FIG. 14.
Figure 16:
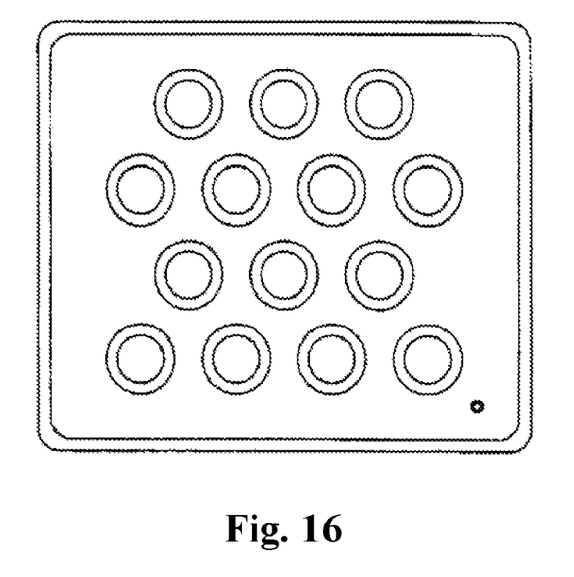
FIG. 16 is the left view of FIG. 14.

As shown in FIGS. 14 through 16, in the fourth embodiment of the present invention, a disinfecting and sterilizing apparatus for liquid and particularly for drinking water, comprises a chamber 1, water pipes 20 provided in the chamber, and ultraviolet lamps 5, wherein the water pipes are made of transparent quartz glass or material penetrable by ultraviolet light and are arranged from top to bottom in five rows, in each of which the water pipes extend and wind to and fro (see FIG. 15) and then bend up and down to the upper or lower row; four rows of totaling fourteen ultraviolet lamp tubes I (it is certainly possible to use only several ultraviolet lamp tubes) are mounted in the inner wall of the chamber with the light tube horizontally inserted between the water pipes; and the inner wall of the chamber is coated with the light-reflecting layer 22.

Figure 17:
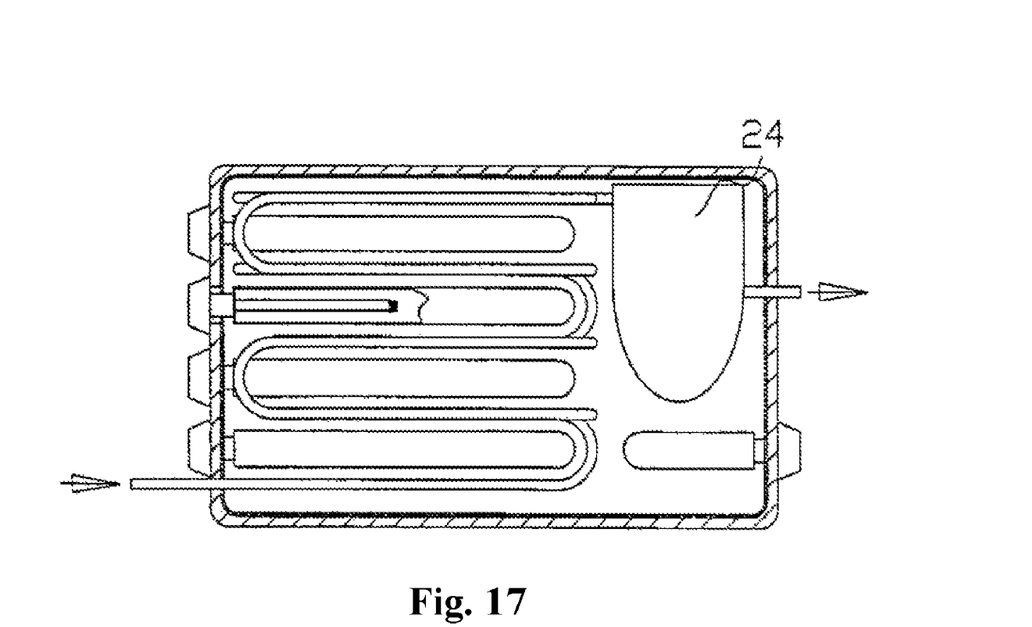
FIG. 17 is the constructional sectional view of the fifth embodiment of the present invention.

As shown in FIG. 17, in the disinfecting and sterilizing apparatus for liquid and particularly for drinking water according to the fifth embodiment of the present invention, the outlet of the water pipe is connected with the filter 24 which is also mounted in the chamber and the filter is on its lower portion mounted with an ultraviolet lamp, which further increases the duration of disinfection and sterilization so as to achieve good effects.

Figure 18:
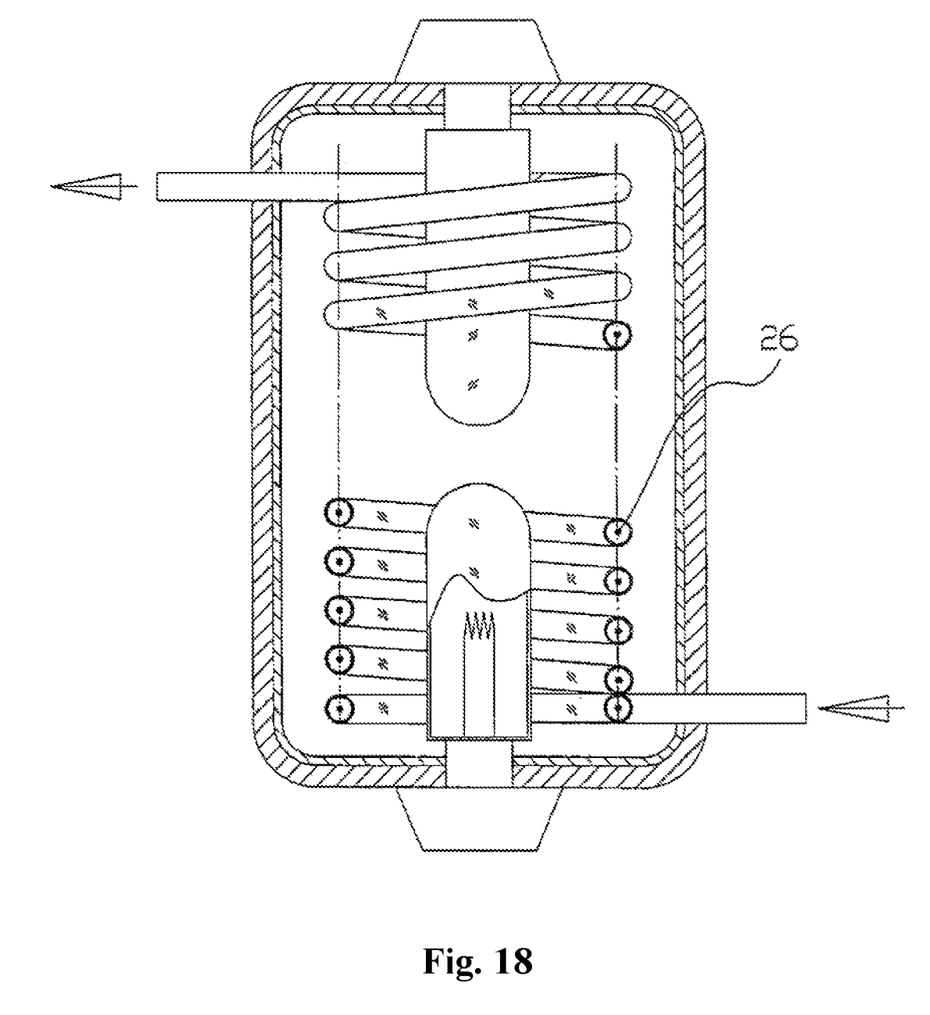
FIG. 18 is the constructional sectional view of the sixth embodiment of the present invention.

As shown in FIG. 18, in the disinfecting and sterilizing apparatus for liquid and particularly for drinking water according to the sixth embodiment of the present invention, the water pipe is spiraled in the form of helix, the ultraviolet lamps are inserted among the water pipes respectively from the top and the bottom, and a metal bar 26 coated with a titanium dioxide layer is placed in the water pipe.

Figure 19:
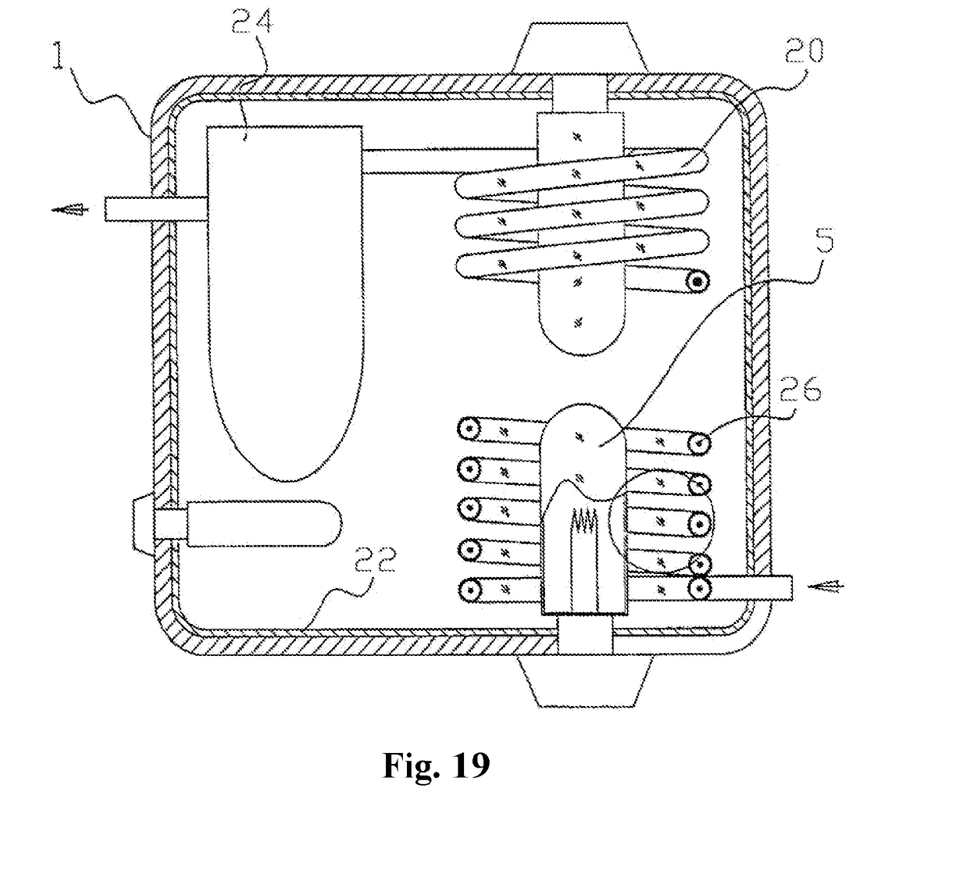
FIG. 19 is the constructional sectional view of the seventh embodiment of the present invention.
Figure 20:
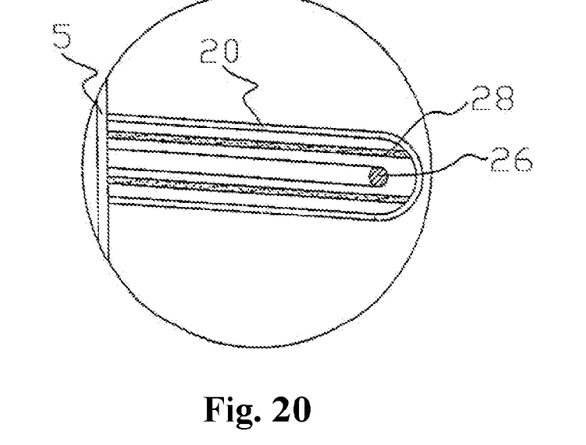
FIG. 20 is the local enlargement view of FIG. 19.

As shown in FIG. 19, in the disinfecting and sterilizing apparatus for liquid and particularly for drinking water according to the seventh embodiment of the present invention, the water pipe is spiraled in the form of helix, the ultraviolet lamps are inserted among the water pipes respectively from the top and the bottom, and a metal bar 26 coated with a titanium dioxide layer is placed in the water pipe, and at the same time two bars 28 coated with titanium dioxide layer are placed on the inner wall of the water pipe.

Figure 21:
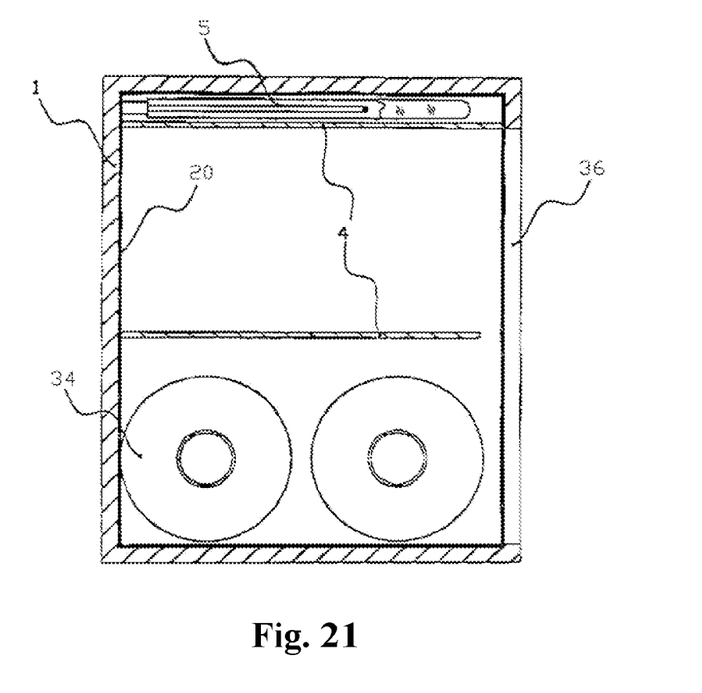
FIG. 21 is the constructional sectional view of the eighth embodiment of the present invention.
Figure 22:
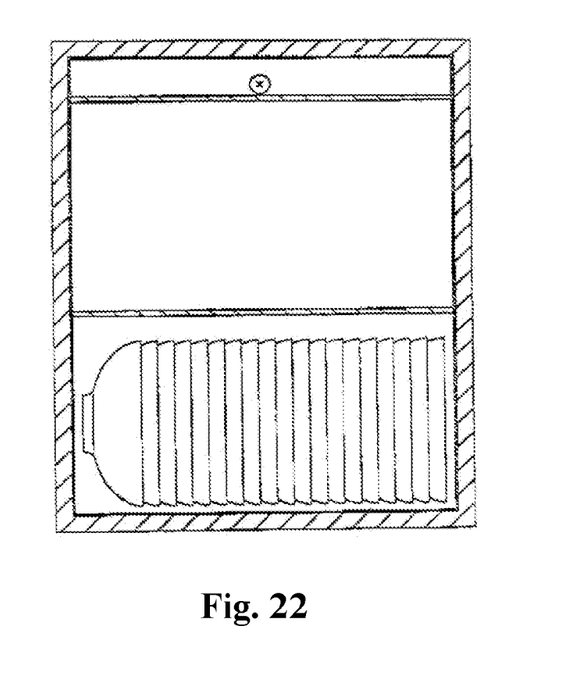
FIG. 22 is the sectional view taken along the line A-A in FIG. 21.

A further variant solution of the present invention, a photocatalytic disinfecting and sterilizing cabinet, is shown in FIGS. 21 and 22, comprising a chamber 1 and a door, wherein the inner wall of the chamber is coated with a titanium dioxide layer 30, and ultraviolet lamps 5, all being of UVC type, are housed in the chamber and mounted in the top portion of the chamber, and are protected by a grid 32.

The dishware 34 is also schematically illustrated in the figures and the position where the door is opened is indicated but the door is not shown. The back surface of the door may be coated with titanium dioxide.

Those skilled in the art should appreciate that various changes and equivalent substitution could be made to the present invention without departing from the spirit and scope of the present invention. Therefore, all such changes and equivalent substitution should be covered in the scope of the present invention for which protection is claimed.

I claim:

1. A combined labyrinthine fluid sterilizing apparatus, comprising a chamber having an inlet and an outlet, the chamber including a blower mounted therein, wherein the blower and the chamber are coated with a layer of titanium dioxide, a lumen of the chamber including an ultraviolet lamp, mounted therein wherein the lumen of the chamber between the inlet and the outlet is divided by at least one baffler, the at least one baffler blocking fluid flow across the lumen from the inlet toward the outlet past the at least one baffler except through a pore disposed offset from a centerline of the lumen, each of the at least one baffler being inserted in a slot provided in the inner side of a front and a back plate of the chamber, a titanium dioxide photocatalyst filter mesh being provided at the pore.

2. The combined labyrinthine fluid sterilizing apparatus according to claim 1, wherein the pore of the baffler is positioned in the upper portion or the lower portion of the baffler and the pores in adjacent bafflers are arranged to stagger up and down.

3. The combined labyrinthine fluid sterilizing apparatus according to claim 1, wherein the pore of the baffler is positioned in a left portion or a right portion of the baffler and the pores in adjacent bafflers are arranged to stagger from side to side.

4. The combined labyrinthine fluid sterilizing apparatus according to claim 1, wherein the slot of the baffler is an inclined slot.

5. The combined labyrinthine fluid sterilizing apparatus according to claim 1, wherein a middle portion of the baffler is in wave shape, a surface of the baffler having distributed thereon titanium dioxide nails.

6. The combined labyrinthine fluid sterilizing apparatus according to claim 1, wherein the baffler is provided with at least one of a positive ion, negative ion, and ionization generator.

7. The combined labyrinthine fluid sterilizing apparatus according to claim 1, wherein the ultraviolet lamp is mounted midway inside at least one of the top plate and the bottom plate of the chamber with the lamp tube horizontally inserted in at least one of the upper and lower midway-indentations of the baffler.

8. The combined labyrinthine fluid sterilizing apparatus according to claim 1, wherein the blower is of the type of a pig cage or a blade.

9. A combined labyrinthine fluid sterilizing apparatus comprising:
    a chamber having an inlet and an outlet the chamber including a blower mounted therein, wherein the blower and the chamber are coated with a layer of titanium dioxide, a lumen of the chamber including an ultraviolet lamp, mounted therein wherein the lumen of the chamber between the inlet and the outlet is divided by at least one baffler, the baffler inserted in a slot provided in the inner side of a front and a back plate of the chamber, the baffler including a pore provided with a titanium dioxide photocatalyst filter mesh, wherein at least one top plate and/or at least one bottom plate have pores and a cover plate wherein the pores and the cover plate of the at least one top plate and/or at least one bottom plate are covered by a shield fixed to at least one of the top plate and the bottom plate, and the cover plate is provided with a raised-cover plate screw passing through the shield.

10. The combined labyrinthine fluid sterilizing apparatus according to claim 9, wherein the pore in one of the bafflers is provided with a one-way openable valve .

11. The combined labyrinthine fluid sterilizing apparatus according to claim 10, wherein the blower is mounted at the pore of the baffler.

* * * * *